(12) United States Patent
Wilzbach

(10) Patent No.: US 8,985,769 B2
(45) Date of Patent: Mar. 24, 2015

(54) METHOD FOR DETERMINING AT LEAST ONE OPTICAL PROPERTY OF A PATIENT EYE WITH AN INTRAOCULAR LENS

(71) Applicant: Carl Zeiss Meditec AG, Jena (DE)

(72) Inventor: Marco Wilzbach, Stuttgart (DE)

(73) Assignee: Carl Zeiss Meditec AG, Jena (DE)

(*) Notice: Subject to any disclaimer, the term of this patent is extended or adjusted under 35 U.S.C. 154(b) by 0 days.

(21) Appl. No.: 14/087,895

(22) Filed: Nov. 22, 2013

(65) Prior Publication Data
US 2014/0078465 A1 Mar. 20, 2014

Related U.S. Application Data

(63) Continuation of application No. PCT/EP2012/059179, filed on May 16, 2012.

(30) Foreign Application Priority Data

May 27, 2011 (DE) .......................... 10 2011 103 360

(51) Int. Cl.
*A61B 3/10* (2006.01)
*A61F 9/007* (2006.01)
(Continued)

(52) U.S. Cl.
CPC .................. *A61B 3/10* (2013.01); *A61B 3/1015* (2013.01); *A61F 9/00736* (2013.01); *A61B 3/103* (2013.01); *A61F 2/16* (2013.01)
USPC ........................................................ 351/205

(58) Field of Classification Search
CPC .. A61B 3/0025; A61B 3/1005; A61B 3/1015; A61B 3/102; A61B 3/12; A61B 3/13; A61F 2/1613

USPC ............... 351/200, 205, 206, 159.02–159.38, 351/159.51; 623/6.11
See application file for complete search history.

(56) References Cited

U.S. PATENT DOCUMENTS 5,709,218 A 1/1998 Holladay et al.
6,749,632 B2 6/2004 Sandstedt et al.
(Continued)

FOREIGN PATENT DOCUMENTS

DE 10 2007 017 599 A1 10/2008
WO WO 99/27334 A1 6/1999

OTHER PUBLICATIONS

Written opinion of the international preliminary examining authority dated May 10, 2013 in international patent application PCT/EP2012/059179 on which the claim of priority is based.
(Continued)

*Primary Examiner* — Mahidere Sahle
(74) *Attorney, Agent, or Firm* — Walter Ottesen P.A.

(57) ABSTRACT

A method determines an optical property (S, C) of a patient eye with an intraocular lens. The patient eye and the intraocular lens define a system. In the method, a measured value of the optical property of the system is determined at a measurement time ($t_M$) after injecting the intraocular lens into the patient eye. The measured value and the associated measurement time ($t_M$) are compared to a known time profile of the values of the optical property for the lens. The known time profile since unfolding the intraocular lens was determined experimentally before the lens is injected and is made available in the form of measurement series or data derived therefrom. A value for the optical property of the system is determined at a different time than the measurement time ($t_M$), according to the known time profile of the values of the optical property for the lens.

10 Claims, 4 Drawing Sheets

(51) Int. Cl.
*A61B 3/103* (2006.01)
*A61F 2/16* (2006.01)

(56) References Cited

U.S. PATENT DOCUMENTS

| | | | |
|---|---|---|---|
| 7,476,248 | B2 | 1/2009 | Harris et al. |
| 7,982,881 | B2 | 7/2011 | Fercher et al. |
| 8,437,008 | B2 | 5/2013 | Fercher et al. |
| 8,550,624 | B2 | 10/2013 | Padrick et al. |
| 2009/0069794 | A1 | 3/2009 | Kurtz |
| 2009/0079935 | A1 | 3/2009 | Harris et al. |
| 2011/0242482 | A1 | 10/2011 | Olsen |

OTHER PUBLICATIONS

Written opinion of the international searching authority dated Aug. 16, 2012 in international patent application PCT/EP2012/059179 on which the claim of priority is based.

International Search Report dated Aug. 16, 2012 of international application PCT/EP2012/059179 on which this application is based.

Oshika, T. et al, "Effect of folding on the optical quality of soft acrylic intraocular lenses.", J Cataract Refract Surg., 1996; 22 Suppl 2: 1360-4. www.ncbi/nlm.nih.gov/pubmed/9051530.

English translation of the Office action of the German Patent Office dated Dec. 23, 2011 in German patent application 10 2011 103 360.6 on which the claim of priority is based.

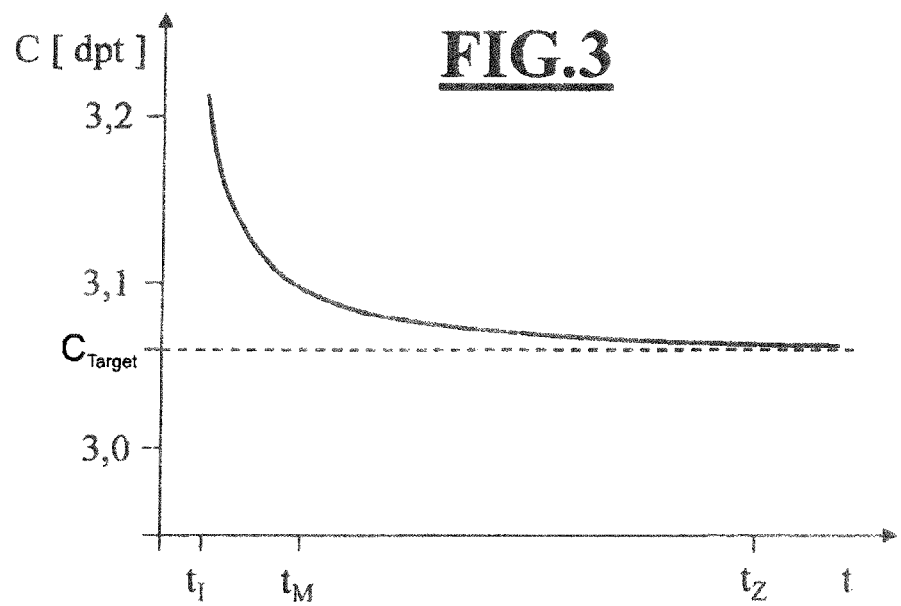
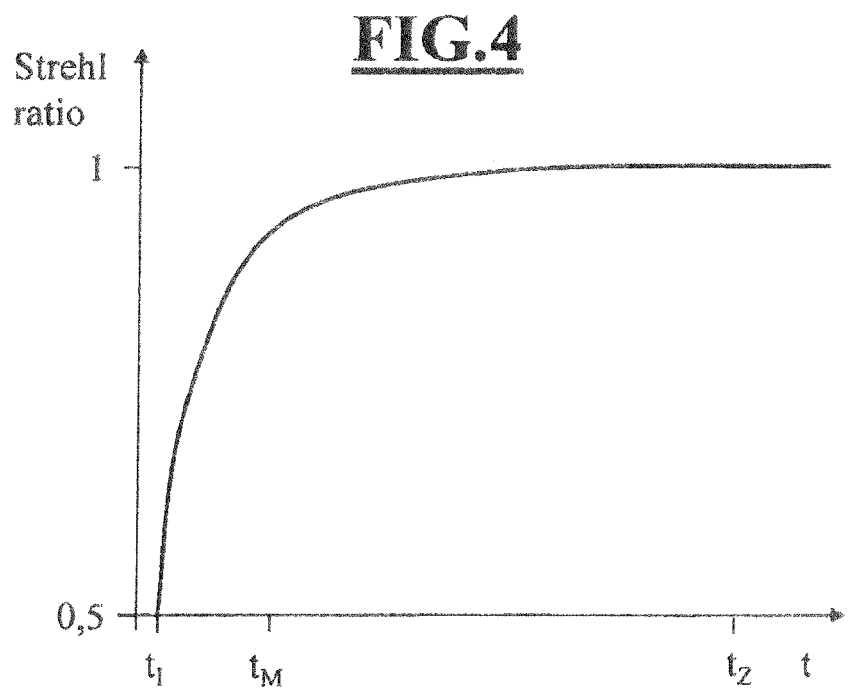

US 8,985,769 B2

METHOD FOR DETERMINING AT LEAST ONE OPTICAL PROPERTY OF A PATIENT EYE WITH AN INTRAOCULAR LENS

CROSS REFERENCE TO RELATED APPLICATIONS

This application is a continuation application of international patent application PCT/EP2012/059179, filed May 16, 2012, designating the United States and claiming priority from German application 10 2011 103 360.6, filed May 27, 2011, and the entire content of both applications is incorporated herein by reference.

BACKGROUND OF THE INVENTION

Intraocular lenses are usually injected into the aphakic eye in a folded state and there they unfold within a matter of seconds. In some cases, anterior chamber intraocular lenses are also injected into the phakic eye. The optical properties of the patient eye are usually measured before and after the surgical procedure. Thus, the medical practitioner obtains no information during the operation with respect to whether the inserted lens can also in actual fact enable the desired visual performance of the patient eye.

Hence, it would be desirable to determine the optical properties of the patient eye with the intraocular lens during surgery. However, such a measurement proves impossible using conventional methods because a number of interfering factors occur during surgery, and these falsify the measurement result. One source of error during the measurement lies in the fact that the optical properties of the intraocular lens change over a period of time of at least fifteen minutes after the injection into the patient eye, during which the intraocular lens completely unfolds. An intraoperative measurement performed within a few minutes after the injection would be falsified as a result of this. Since conventional cataract surgery only takes approximately five to ten minutes, it however proves not to be possible to wait in the case of the intraoperative measurement of an implanted intraocular lens until the optical properties have reached their final value.

DE 10 2007 017 599 A9 describes a method for measuring geometric parameters of an eye in order to determine a fitting intraocular lens, for example also for an eye which, as a result of preceding refractive corneal surgery, has modified relationships between the front side of the cornea and the back side of the cornea.

U.S. Pat. No. 7,476,248 and U.S. patent application publication 2009/0079935 describe a method for predicting changes in the patient eye caused by the operation. Here, changes of the eye, for example, a deformation of the cornea as a result of the incisions performed during the operation, are used in the calculation of the optical properties of the intraocular lens.

U.S. Pat. Nos. 8,437,008 and 7,982,881 describe a device for measuring a sample, more particularly an eye, by interferometry.

U.S. patent application publication 2009/0069794 describes an instrument for laser eye surgery, wherein the surgical laser beam is focused as accurately as possible onto the target tissue.

SUMMARY OF THE INVENTION

In view of the foregoing, it is an object of the invention to provide a method for determining at least one optical property of a patient eye with an intraocular lens during surgery, with it being possible to determine the optical property with great accuracy.

A method for determining at least one optical property of a patient eye with an intraocular lens comprises the steps of:

determining at least one measured value of the optical property of the system comprising patient eye and intraocular lens at at least one measurement time after injecting the intraocular lens into the patient eye, wherein, at the measurement time, a change in the at least one optical property of the intraocular lens after the injection has not yet been completed;

comparing the at least one measured value and the associated measurement time to a known time profile of the values of the optical property for the intraocular lens, wherein the known time profile since unfolding the intraocular lens has been determined experimentally before the intraocular lens is injected and is made available in the form of measurement series or data, formulae or tables derived therefrom; and, determining a value for the optical property of the system comprising patient eye and intraocular lens at a different time than the measurement time, according to the known time profile of the values of the optical property for the intraocular lens.

Here, the known time profile of the values of the optical property was determined in advance for the utilized intraocular lens. To this end, an intraocular lens manufacturer can, for example, carry out test series in order to establish the time profile of the optical properties for a specific model or for a specific batch of intraocular lenses after the lens unfolds. The results of these test series, or data, formulae or tables derived therefrom are then used during the method according to the invention as known time profile.

Thus, the method according to the invention can be used to establish a final value of the optical property with great accuracy already at a measurement time at which the change in the at least one optical property of the intraocular lens after the injection has not yet been completed. The known time profile makes it possible to convert a measured value, which was determined shortly after the intraocular lens was injected into the patient eye, into a target value for the optical property which will be present after the intraocular lens has completely unfolded and relaxed in the patient eye. Thus, it is already possible to make a precise prediction of the optical property of the patient eye with the injected intraocular lens during the operation. As a result, it is possible to perform possible adjustments of the eye or the intraocular lens in order to enable an improved visual performance.

In this case, the intraocular lens can be injected into the patient eye in a folded state and unfold in the patient eye from the time of the injection. Alternatively, other implantation methods for the intraocular lens are also feasible, in which the intraocular lens is injected into the patient eye in, for example, a rolled or otherwise deformed state.

The at least one measured value can be determined by means of a wavefront measurement. Such a measurement method is known for pre- and postoperative determination of the optical properties of the patient eye and makes it possible to determine the measured value with great accuracy. However, in principle, the present invention is not restricted to a specific measurement method and how the measured values of the patient eye with the intraocular lens and the time profile of the values for the intraocular lens were measured is irrelevant to determining the value of the optical property that will be present after the intraocular lens has completely unfolded.

The at least one optical property can comprise values for the spherical correction, the cylindrical correction and/or a Strehl ratio of the system comprising patient eye and intraocular lens. Here, the most important parameters for the sight of the patient can be determined during the operation with aid of the spherical correction and the cylindrical correction, and so corrections can still be undertaken if required in order to improve the sight of the patient present after the operation.

The Strehl ratio specifies the optical quality of the system comprising intraocular lens and patient eye, and so the method according to the invention can be used to identify defects of the intraocular lens, which impair the optical quality (for example, as a result of dispersion on a damaged surface of the lens), already during the operation.

The at least one measured value can be determined within a time interval of less than five minutes, more particularly within a time interval of less than one minute, after the injection of the intraocular lens. As a result of measuring the at least one optical property as quickly as possible, a longer period of time remains for the medical practitioner to perform corrections in respect of the optical properties of the patient eye, given a predetermined maximum duration of the cataract operation. By way of example, such a correction can comprise a replacement of the intraocular lens, or corrections that influence the optical properties of the cornea can be performed on the cornea.

The value established from the at least one measured value and the time profile of the optical property can specify a final value of the optical property, which is approached by the time profile. This enables a prediction of the final sight of the patient eye on the basis of the measured value determined shortly after the intraocular lens was injected.

The time profile of the optical property can be described by an exponential function of the form:

$$S(t)=a1-b1*\exp(-c1*t)$$

or $$C(t)=a2+b2*\exp(-c2*t),$$

with S being a spherical correction and C being a cylindrical correction of the system comprising patient eye and intraocular lens, and with a1, a2, b1, b2, c1 and c2 specifying constants which were determined by a curve fit to experimentally determined data of the optical property of the intraocular lens as a function of the time t elapsed since unfolding. In addition to the time profile of the spherical correction and the cylindrical correction, it is also possible to approximate the time profile of further optical properties of the intraocular lens by means of suitable functions.

Furthermore, provision is made for a computer program product which contains program code which, when executed by a processor of a computer, carries out the method described above.

A device for determining at least one optical property of a patient eye with an intraocular lens comprises:
  means for determining at least one measured value of the optical property of the system comprising patient eye and intraocular lens at at least one measurement time after injecting the intraocular lens into the patient eye, wherein, at the measurement time, a change in the at least one optical property of the intraocular lens after the injection has not yet been completed;
  means for comparing the at least one measured value and the associated measurement time to a known time profile of the values of the optical property for the intraocular lens, wherein the known time profile since unfolding the intraocular lens has been determined experimentally before the intraocular lens is injected and is made available in the form of measurement series or data, formulae or tables derived therefrom; and,
  means for determining a value for the optical property of the system comprising patient eye and intraocular lens at a different time than the measurement time, according to the known time profile of the values of the optical property for the intraocular lens.

The device thus enables intraoperative determination of the optical property of the intraocular lens with high accuracy because interference factors that can be traced back to the temporal change of the optical property after the intraocular lens unfolds can be eliminated.

The present invention furthermore provides a surgical microscope which comprises a device as described above. Here, the surgical microscope can furthermore comprise a device for establishing the at least one optical property by means of a wavefront measurement.

BRIEF DESCRIPTION OF THE DRAWINGS

The invention will now be described with reference to the drawings wherein:

FIG. 3 shows a typical time profile of a cylindrical correction of the intraocular lens after injection into a patient eye;

FIG. 4 shows a typical time profile of a Strehl ratio of the intraocular lens after injection into a patient eye;

DESCRIPTION OF THE PREFERRED EMBODIMENTS OF THE INVENTION

Figure 1:
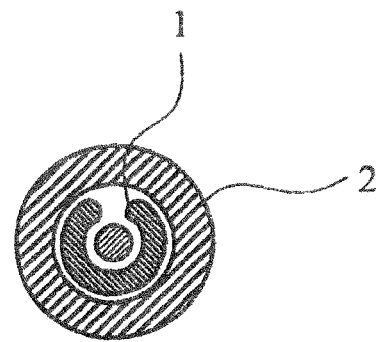
FIG. 1 is a schematic of an intraocular lens in an injection device.

As shown schematically in FIG. 1, an intraocular lens 1 is accommodated in an injection device 2 by means of which the intraocular lens 1 can be injected into a patient eye. The intraocular lens 1 is folded or rolled up in the injection device 2, that is, elastically deformed.

In order to avoid a plastic deformation of the intraocular lens 1, the intraocular lens is usually stored in an unfolded state and only introduced into the injection device 2 shortly before the injection and folded in the process. In the example shown, the intraocular lens 1 is a toric lens, but the method according to the invention can also be applied to different types of intraocular lens.

After leaving the injection device 2, the intraocular lens 1 unfolds in the patient eye. While the intraocular lens 1 in the process substantially reassumes its original shape within a few seconds, the optical properties of the intraocular lens relax significantly more slowly.

In the present embodiment, the optical properties of the patient eye or the intraocular lens 1 are measured during surgery by a wavefront measurement method. The particular time profile of the optical properties of the intraocular lens is also determined by a wavefront measurement in the present embodiment.

Figure 2:
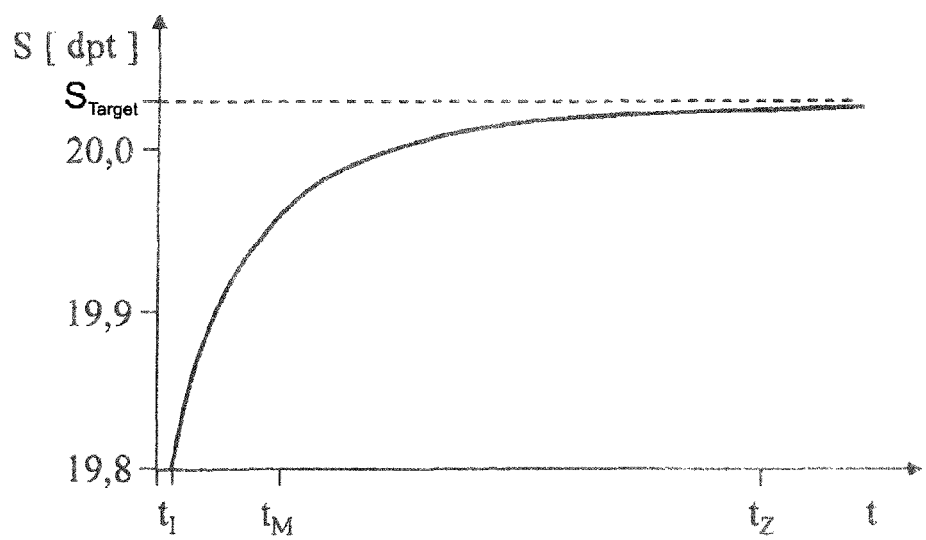
FIG. 2 shows a typical time profile of a spherical correction of the intraocular lens after injection into a patient eye.

FIG. 2 shows an example for the time profile for the spherical correction S of the intraocular lens 1 in diopters from the time $t_I$ of the injection into the patient eye.

As shown in FIG. 2, the spherical correction S of the intraocular lens asymptotically approaches a final value $S_{Target}$ with increasing time. The period of time elapsed until a substantially constant value is reached is at least fifteen minutes.

The experimentally determined time profile, shown in FIG. 2, can, in this case, be stored as a table of measured values, or it is possible, for example, to fit an exponential function of the form $$S(t)=a1-b1*\exp(-c1*t)$$

to the measured values, with a1, b1 and c1 being constants.

Such a time profile of the spherical correction and other optical properties can be determined experimentally for each model and/or for each individual batch of intraocular lenses 1. By way of example, the manufacturer of the intraocular lenses performs this determination. The time profile of the values after the intraocular lens unfolds can then be offered by the manufacturer together with the corresponding intraocular lens, and so a medical practitioner can, during the intraoperative measurement of the system comprising patient eye and intraocular lens, refer to the data in respect of the time profile provided by the manufacturer.

If a measured value for the spherical correction S of the system comprising patient eye and intraocular lens is determined at a measurement time $t_M$ after the injection in the case of an intraocular lens 1 for which the time profile of the spherical correction S was already determined, a value for any desired target time $t_Z$ can thus be established for the spherical correction S of the system comprising patient eye and intraocular lens from the known time profile of the values for the intraocular lens and the measured value at the time $t_M$.

In particular, this enables the final value of the spherical correction S to be determined already a few seconds after injecting the intraocular lens 1 into the patient eye, which final value will be present after complete unfolding and relaxation of the optical properties of the intraocular lens 1.

FIG. 3 shows an example for a time profile for the cylindrical correction C in diopters from a time $t_I$ of the injection of the intraocular lens 1 into the patient eye.

As described above in the context of the time profile of the spherical correction S of the intraocular lens 1, the value of the cylindrical correction. C of the intraocular lens 1 also relaxes to a substantially constant final value $C_{Target}$ over a period of time of at least fifteen minutes.

It is also possible in this case for the time profile of the cylindrical correction C, determined experimentally in advance by the manufacturer, to be stored as a table of measured values, or it is possible for example to fit an exponential function of the form $$C(t)=a2+b2*\exp(-c2*t)$$

to the measured values, with a2, b2 and c2 being constants.

Thus, it is also possible to determine a measured value at a measurement time $t_M$ for the cylindrical correction C of the system comprising patient eye and intraocular lens already a few seconds after the time $t_I$ of the injection, from which measured value the target value of the cylindrical correction C for the patient eye with intraocular lens can then be calculated with the aid of the known time profile of the values for the intraocular lens.

FIG. 4 shows the time profile of a Strehl ratio of the intraocular lens 1 from a time $t_I$ of the injection into the patient eye. The Strehl ratio describes the ratio between the part of the light energy which an optical system actually unifies in the diffraction disc and the light energy which an error-free system would unify there. Hence, measuring the Strehl ratio makes it possible to check the optical quality of the injected intraocular lens 1.

As described above in the context of the spherical correction, the known time profile for the Strehl ratio can also, for example, be approximated by an exponential function. A measured value of the Strehl ratio of the system comprising patient eye and intraocular lens determined at a measurement time $t_M$ can then be converted into a final value, which will be present at a time $t_Z$, with the aid of the known time profile.

Hence problems in respect of the quality of the intraocular lens 1 can already be reliably detected a few seconds after the injection if the calculated, final value of the Strehl ratio lies under the expected value for this model or this batch of intraocular lenses. As a result, the medical practitioner still has sufficient time during the operation to replace a defective intraocular lens 1 if necessary.

Figure 5:
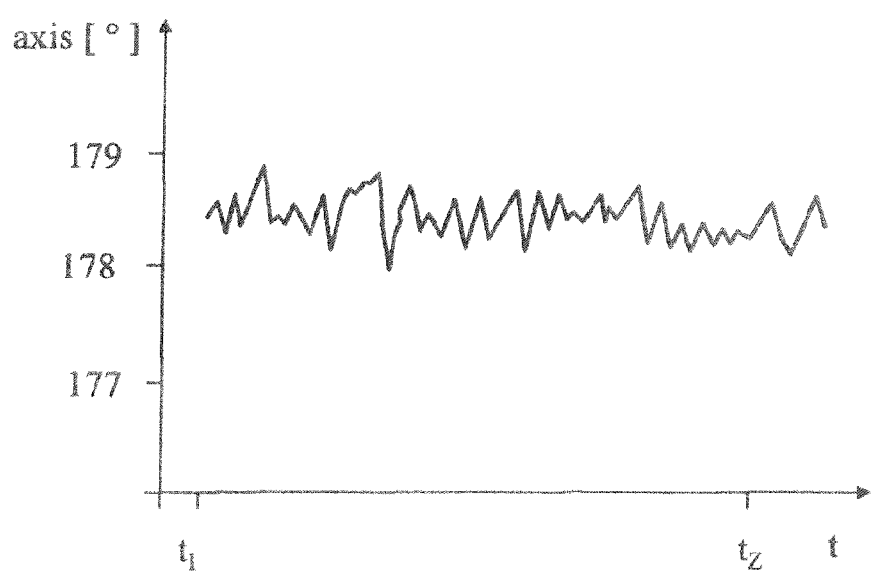
FIG. 5 shows a typical time profile of the alignment angle of the cylindrical axis of the intraocular lens after injection into a patient eye.

FIG. 5 shows that, in the case of the intraocular lens 1 considered in an exemplary fashion, the alignment of the cylinder axis remains substantially constant during the unfolding and the relaxation of the remaining optical properties.

Hence, the alignment of the cylinder axis of the system comprising patient eye and intraocular lens can be measured at any time after the injection for this intraocular lens 1 and it is unnecessary for the shown intraocular lens 1 also to correct this measured value using a known time profile. However, it is feasible that the alignment of the cylinder axis could also change over time in the case of other intraocular lenses 1 such that the method described above can then also be applied for this optical property.

Here, a method according to an embodiment of the present invention initially comprises the insertion of an intraocular lens 1 into an injection device 2 and the injection of the intraocular lens 1 into a patient eye at an injection time $t_I$.

A wavefront measurement method is then used at a measurement time $t_M$, which is a few seconds after the injection time $t_I$, to determine optical properties such as, for example, the spherical correction S, the cylindrical correction C and/or the Strehl ratio of the patient eye with injected intraocular lens 1.

The measured values determined at the measurement time $t_M$ and the known time profiles of the optical properties are used to calculate final values for the optical properties. In this case, "final values" are understood to mean those values which the particular time profile of the optical properties asymptotically approaches for long periods of time after the injection time $t_I$. In general, the value of the optical property still changes relatively rapidly during the first approximately ten minutes after the injection, and the rate of change over time reduces from approximately fifteen minutes after the injection such that the value of the optical property then gradually approaches its constant target value.

Alternatively, it is also possible to set a fixed target time $t_Z$, for example thirty minutes or sixty minutes after $t_I$, and the values of the optical properties can be determined for this target time $t_Z$. This procedure is advantageous, particularly if no function was fitted to the measured values made available by the manufacturer of the intraocular lens 1 and hence it is not readily possible to determine a target value to which the optical property converges.

Here, it is also possible to provide a plurality of measurement times $t_M$, for example, five measurement times each at a spacing of a few seconds, and to determine measured values for the optical properties for each measurement time $t_M$. As a result of the fact that a temporal sequence of measured values is determined, the measured time profile of the measured values of the optical properties can be compared to the time profile determined in advance. By way of example, this makes it possible to identify damage to the injected intraocular lens in a quick and reliable manner if it turns out that the time profile of the values for the optical properties, determined by the plurality of measured values, strongly differs from the corresponding time profiles for this model, that is, this batch of intraocular lenses 1 determined in advance.

Finally, the determined values for the optical properties are output, for example by means of a display device, and the medical practitioner can use these displayed values to determine the quality of the injected intraocular lens and the patient eye operated on with great accuracy. Hence, it is already possible to perform corrections on the patient eye at a time during the operation at which the intraocular lens 1 has not yet reached the final values of its optical properties.

The method according to the invention enables the medical practitioner to determine these final values already a few seconds after the injection of the intraocular lens into the patient eye and hence after a few seconds to already obtain precise data in respect of the final visual performance of the patient eye operated on.

Figure 6:
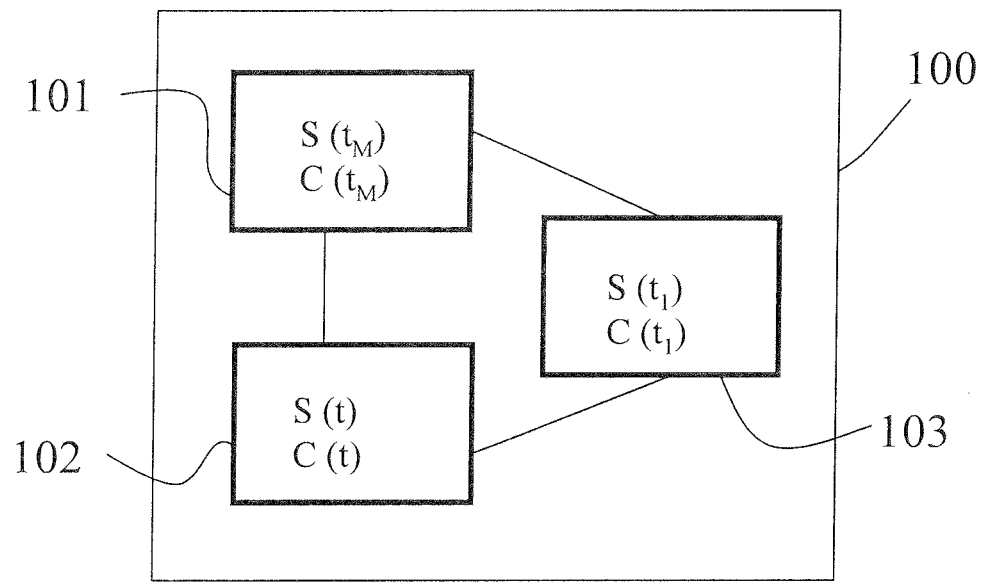
FIG. 6 is a schematic of a device for determining at least one optical property of a patient eye with an intraocular lens; and, FIG. 7 is a schematic of a surgical microscope comprising the device for determining at least one optical property.

FIG. 6 illustrates a device 100 for determining at least one optical property such as spherical correction S and cylindrical correction C of a patient eye with an intraocular lens. The device comprises means 101 for determining at least one measured value of the optical property such as $S(t_M)$ or $C(t_M)$ of the system comprising patient eye and intraocular lens at at least one measurement time $t_M$ after injecting the intraocular lens into the patient eye. Furthermore, the device 100 comprises means 102 for comparing the at least one measured value and the associated measurement time $t_M$ to a known time profile of the values of the optical property such as $S(t)$ and $C(t)$ for the intraocular lens, wherein the known time profile since unfolding the intraocular lens has been determined experimentally before the intraocular lens 1 is injected and is made available in the form of measurement series or data, formulae or tables derived therefrom. In addition the device 100 comprises means 103 for determining a value for the optical property such as $S(t_1)$ and $C(t_1)$ of the system comprising patient eye and intraocular lens 1 at a different time $t_1$ than the measurement time $t_M$, according to the known time profile of the values of the optical property spherical correction and cylindrical correction for the intraocular lens 1.

Figure 7:
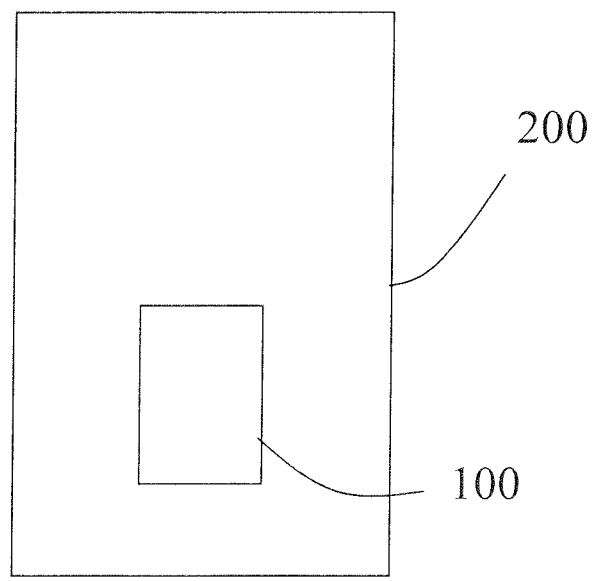

FIG. 7 is a schematic representation of a surgical microscope 200 comprising the device 100.

It is understood that the foregoing description is that of the preferred embodiments of the invention and that various changes and modifications may be made thereto without departing from the spirit and scope of the invention as defined in the appended claims.

What is claimed is:

1. A method for determining at least one optical property (S, C) of a patient eye with an intraocular lens wherein the patient eye and the intraocular lens define a system, the method comprising the steps of:

determining at least one measured value of the optical property (S, C) of the system at at least one measurement time ($t_M$) after injecting the intraocular lens into the patient eye, wherein, at the measurement time ($t_M$), a change in the at least one optical property (S, C) of the intraocular lens after the injection has not yet been completed;

comparing the at least one measured value and the measurement time ($t_M$) corresponding thereto to a known time profile of the values of the optical property (S, C) for the intraocular lens, wherein the known time profile since unfolding the intraocular lens has been determined experimentally before the intraocular lens is injected and is made available in the form of measurement series or data, formulae or tables derived therefrom; and, determining a value for the optical property (S, C) of the system at a different time than the measurement time ($t_M$), according to the known time profile of the values of the optical property (S, C) for the intraocular lens.

2. The method of claim 1, wherein said at least one optical property (S, C) comprises a spherical correction (S), a cylindrical correction (C) and/or a Strehl ratio of the intraocular lens.

3. The method of claim 2, wherein said at least one measured value is determined within a time interval of less than five minutes after the injection of the intraocular lens.

4. The method of claim 3, wherein said at least one measured value is determined within a time interval of less than one minute after the injection of the intraocular lens.

5. The method of claim 3, wherein the value established from the at least one measured value and the time profile of the optical property (S, C) provides a final value of the optical property (S, C) which is approached by the time profile.

6. The method of claim 4, wherein the time profile of the optical property (S, C) is described by an exponential function of the form:

$$S(t)=a1-b1*\exp(-c1*t)$$

or $$C(t)=a2+b2*\exp(-c2*t),$$

wherein a1, a2, b1, b2, c1 and c2 are constants which were determined by a curve fit to experimentally determined data of the optical property (S, C) of the intraocular lens as a function of the time elapsed since unfolding.

7. A computer program product containing a program code which, when executed by a processor of a computer, carries out a method for determining at least one optical property (S, C) of a patent eye with an intraocular lens wherein the patient eye and the intraocular lens define a system, the method comprising the steps of:

determining at least one measured value of the optical property (S, C) of the system at at least one measurement time ($t_M$) after injecting the intraocular lens into the patient eye, wherein, at the measurement time ($t_M$), a change in the at least one optical property (S, C) of the intraocular lens after the injection has not yet been completed;

comparing the at least one measured value and the measurement time ($t_M$) corresponding thereto to a known time profile of the values of the optical property (S, C) for the intraocular lens, wherein the known time profile since unfolding the intraocular lens has been determined experimentally before the intraocular lens is injected and is made available in the form of measurement series or data, formulae or tables derived therefrom; and, determining a value for the optical property (S, C) of the system at a different time than the measurement time ($t_M$), according to the known time profile of the values of the optical property (S, C) for the intraocular lens.

8. A device for determining at least one optical property (S, C) of a patient eye with an intraocular lens wherein the patient eye and the intraocular lens define a system, the device comprising:

means for determining at least one measured value of the optical property (S, C) of the system at at least one measurement time ($t_M$) after injecting the intraocular lens into the patient eye, wherein, at the measurement time ($t_M$), a change in the at least one optical property (S, C) of the intraocular lens after the injection has not yet been completed;

means for comparing the at least one measured value and the measurement time ($t_M$) corresponding thereto to a known time profile of the values of the optical property (S, C) for the intraocular lens, wherein the known time profile since unfolding the intraocular lens has been determined experimentally before the intraocular lens is injected and is made available in the form of measurement series or data, formulae or tables derived therefrom; and, means for determining a value for the optical property (S, C) of the system at a different time than the measurement time ($t_M$), according to the known time profile of the values of the optical property (S, C) for the intraocular lens.

9. A surgical microscope comprising:

a device for determining at least one optical property (S, C) of a patient eye with an intraocular lens wherein the patient eye and the intraocular lens define a system, the device including:

means for determining at least one measured value of the optical property (S, C) of the system at at least one measurement time ($t_M$) after injecting the intraocular lens into the patient eye, wherein, at the measurement time ($t_M$), a change in the at least one optical property (S, C) of the intraocular lens after the injection has not yet been completed;

means for comparing the at least one measured value and the measurement time ($t_M$) corresponding thereto to a known time profile of the values of the optical property (S, C) for the intraocular lens, wherein the known time profile since unfolding the intraocular lens has been determined experimentally before the intraocular lens is injected and is made available in the form of measurement series or data, formulae or tables derived therefrom; and, means for determining a value for the optical property (S, C) of the system at a different time than the measurement time ($t_M$), according to the known time profile of the values of the optical property (S, C) for the intraocular lens.

10. The surgical microscope of claim 9, furthermore comprising a device for establishing the at least one optical property by means of a wavefront measurement.

* * * * *

UNITED STATES PATENT AND TRADEMARK OFFICE
CERTIFICATE OF CORRECTION

PATENT NO. : 8,985,769 B2
APPLICATION NO. : 14/087895
DATED : March 24, 2015
INVENTOR(S) : Marco Wilzbach It is certified that error appears in the above-identified patent and that said Letters Patent is hereby corrected as shown below:

In the Specification

In Column 5:

Line 17: delete "$S(t) = a1 - b1 * \exp(-c * t)$" and substitute -- $S(t) = a1 - b1 * \exp(-c1 * t)$ -- therefor.

Signed and Sealed this
Eighth Day of September, 2015

Michelle K. Lee
*Director of the United States Patent and Trademark Office*